United States Patent [19]

Dieterich

[11] 4,263,902
[45] Apr. 28, 1981

[54] ORTHOPEDIC SANDAL

[76] Inventor: Alfred Dieterich, Westtorgraben 3, 8500 Nuremberg, Fed. Rep. of Germany

[21] Appl. No.: 940,864

[22] Filed: Sep. 8, 1978

[30] Foreign Application Priority Data

Sep. 14, 1977 [DE] Fed. Rep. of Germany ....... 2741302
May 30, 1978 [DE] Fed. Rep. of Germany ....... 2823478

[51] Int. Cl.³ ............................................... A61F 5/00
[52] U.S. Cl. .................................. 128/81 R; 128/581; 128/25 B
[58] Field of Search .............. 128/80 R, 80 DB, 81 R, 128/80 G, 581, 582, 153, 25 B; 36/11.5

[56] References Cited

U.S. PATENT DOCUMENTS

| 1,055,810 | 3/1913 | Scholl | 128/81 R |
|---|---|---|---|
| 1,730,466 | 10/1929 | Mallott | 128/81 R |
| 1,996,614 | 4/1935 | Davis | 128/25 B |
| 2,153,968 | 4/1939 | Loufbahn | 36/11.5 |
| 2,187,920 | 1/1940 | Triplett | 128/25 B |
| 2,265,853 | 12/1941 | Nussbaum | 128/581 |
| 2,948,972 | 8/1960 | Anderson | 128/581 |
| 3,299,893 | 1/1967 | Collina | 128/581 |
| 3,308,829 | 3/1967 | Edwards | 128/80 R |

FOREIGN PATENT DOCUMENTS

| 480291 | 7/1929 | Fed. Rep. of Germany | 128/81 R |
|---|---|---|---|
| 928087 | 5/1955 | Fed. Rep. of Germany | 128/81 R |
| 887782 | 11/1943 | France | 36/11.5 |
| 935109 | 6/1948 | France | 128/81 R |
| 126918 | 4/1927 | Switzerland | 128/81 R |

Primary Examiner—Robert W. Michell
Assistant Examiner—Arthur S. Rose
Attorney, Agent, or Firm—Holman & Stern

[57] ABSTRACT

An orthopedic sandal for correction of hammer-toes and X-toe (Halux Valgus) being a dual lever arm arrangement pivotable on a horizontal axis transverse to the sole. A pressure element for pressing the toes downward is on one arm and the other arm is fastened to the rearward portion of the foot so that as the foot is lifted, the pressure element is pressed downwardly on the hammer-toes.

Additionally, several mechanisms for correcting X-toe can operate in conjunction with the lever arm arrangement. A strap loop can be pulled by the movement of the pressure element. A two-chamber hydraulic pneumatic system actuated by the pressure element pressing the hammer-toes can push on the X-toe. An elastic resilient member can push the X-toe. A fourth mechanical mechanism using a nut-and-threaded shaft to turn a paddle pushing the X-toe can be actuated by foot pressure on a flexible pad in the sole. The pressure on the hammer-toes can be adjusted depending on the fulcrum point of the lever arm arrangement. The pressure on the X-toe can be arranged to be continuous with augmentation whenever the lever arm arrangement is operated.

27 Claims, 15 Drawing Figures

ORTHOPEDIC SANDAL

BACKGROUND OF THE INVENTION

The instant invention concerns an orthopedic sandal which is provided with a device for the corrective treatment of hammer-toes.

Hammer-toes are defined to be partially-stiff toes where the basic joints of the toes are in an overstretched position and the middle and end joints are in a bent position and are either partially or totally stiff. Previously the successful treatment of hammer-toes was only possible by means of surgery. One type of sandal, however, is known in the art in which a thin aluminum plate is placed from the top onto the stretch-contraction of the toes. An elastic rubber-band is guided around this plate and below the bottom surface of the sandal and is stretched. The stress force of this rubber-band should stretch the hammer-toes. However, when the pressure is heavy enough to effect the treatment, blood circulation is cut off. It is furthermore disadvantageous that at the moment of the main stress on the front portion of the foot, i.e., during walking, the pressure of the device is released.

It is an object of the present invention to provide a sandal suitable for a successful corrective treatment of hammer-toes. Additionally, the sandal is suitable for intermittent treatment of this condition. It is a further object to effect simultaneously with the treatment of hammer-toes, a correcting of the conditions of so-called X-toe (Hallux Valgus) and splay foot.

SUMMARY OF THE INVENTION

In order to solve this problem, the present invention firstly comprises a dual-armed lever arrangement for the treatment of hammer-toes. The lever arrangement is pivoted on the sandal on a horizontally extending axis which is somewhat transverse to the longitudinal axis of the foot when the foot is placed on the sandal. One of the lever arms of the lever arrangement is provided with a pressure element which, when the foot rests on the sandal, is located above the base joints and the center joints of the toes. The other lever arm of the lever arrangement can be fastened to the rearward portion of an emplaced foot. The lever arrangement is constructed in a fashion so that a lifting upwards of the lever arm being connected with the rearward portion of the foot will effect pressing the pressure element onto the base joints and center joints of the toes. Such a type of sandal can be manufactured with simple means and therefore at economical costs. The corrective treatment of hammer-toes is thereby simple and effective. The foot is placed onto the surface of the sandal, the toes being located in the correct position in relation to the pressure element. By lifting off the rearward portion of the foot, one will be able to press the pressure element onto the hammer-toes in the sense of stretching and thus producing a more normal position for the toes. This lifting upwards of the heel may be produced by the process of walking. However, this type of pressure on the toes may also be produced while standing or in a sitting position by respectively lifting upwards the heel area of the foot. Additionally, it is also possible by pulling tighter and locking an ankle bandage or the like of the sandal, which will be explained in more detail hereinbelow, and thusly effecting a pulling upwards of the lever arm connected thereto, to obtain an additional constant and corrective pressure of the pressure element on the hammer-toes.

According to a preferred embodiment, the pivot point of the lever arrangement may be adjustable in the longitudinal direction of the sandal, wherein, however, the entire length of the lever arrangement remains unchanged. This changing of the transformation ratio of both lever arms reduces or increases the pressure on the hammer-toes during simultaneous lifting upwards of the heel.

In all of the above-described cases, it is possible for a person to determine and thereby regulate the strength of pressure on the toes. The above explained possibilities of the correcting influence may have an effect either in and of themselves or in combination with each other. The conservative treatment of hammer-toes is intermittent with the present invention. The pressure becoming effective either instantly or intermittently in contrast to the above-described prior art sandal, can be endured by the patient; especially since this pressure, as above explained, can be adjusted by the patient. There exists no danger of cutting off the blood circulation. The present invention represents to the patient a substantial improvement with regard to time and money, since formerly such an intermittent treatment was possible only by means of physical therapy. The treatment costs necessary for physical therapy are many times higher than the purchasing price of such a sandal. It has been proven that it is difficult for a patient, and also is connected with a tremendous expenditure of time, to subject oneself regularly to a physical therapy treatment. In contrast therewith, the patient is able to wear the inventive sandal at any suitable occasion. The utilization of the inventive sandal has an influence on the front portion and the toes of the foot which counteracts the damaging effects caused by modern shoes which are pointed at the front and having heels which are excessively high.

An X-toe (Hallux Valgus) is a large toe which is partially stiffened in its base joint, with a deviation of its position toward the outer side of the foot and in many instances may be pointed upward to some extent. The present invention can further on the front area of the sole be provided a means for correcting the X-position of the large toe and to be in an effective connection with the pressure element so that a downwards movement of the pressure element causes the large toe to perform a medial movement, that is, one towards the inner (arch) side of the foot.

Similar conservative treatment possibilities existed formerly only in the form of daily bandagings and by nightly applications of a splint, exclusively for the separate treatment of the HALUX VALGUS. X-toes appear however mostly in combination with hammer-toes, so that, by means of the present invention, they can be treated simultaneously with the inventive conservative treatment of the hammer-toes. As soon as with the lifting upwards of the heel the above-explained lever effect begins to function, also the respective large toe is pulled inwards. In this connection it should also be considered that in general, the large toe is not a hammer-toe but represents only the aforementioned X-toe, while in contrast the toes number II to V are generally hammer-toes. Thus, all toes are optimally being treated.

Furthermore, hammer-toes and X-toes appear mostly in connection with a pronounced splay foot. A splay foot represents a deformation of the front portion of the foot, whereby the transversal arch which is located somewhat behind the center metatarsal heads I–V no longer extend convex upwardly, but run convexly downwardly, whereby the transverse diameter of the frontal portion of the foot is widened. For this reason, the present invention can further comprise the sole of the sandal being provided with a longitudinal arch at the point of emplacement surface, similar to a corrective orthopedic insert of a shoe, and most of all having a strongly-shaped transverse arching (splay foot pelotte). When weight is placed on the sole of the sandal this produces not only a corrective influence on the splay foot position, but by means of this splay foot pelotte there is also provided a simultaneous support of the correcting influence of the sandal on the hammer-toes.

BRIEF DESCRIPTION OF THE DRAWINGS

Further advantages and characteristics of the present invention may be seen from the dependent claims as well as from the following disclosure and the pertinent drawings of the inventive embodiments, wherein:

DETAILED DESCRIPTION OF THE PREFERRED EMBODIMENTS

Figure 1:
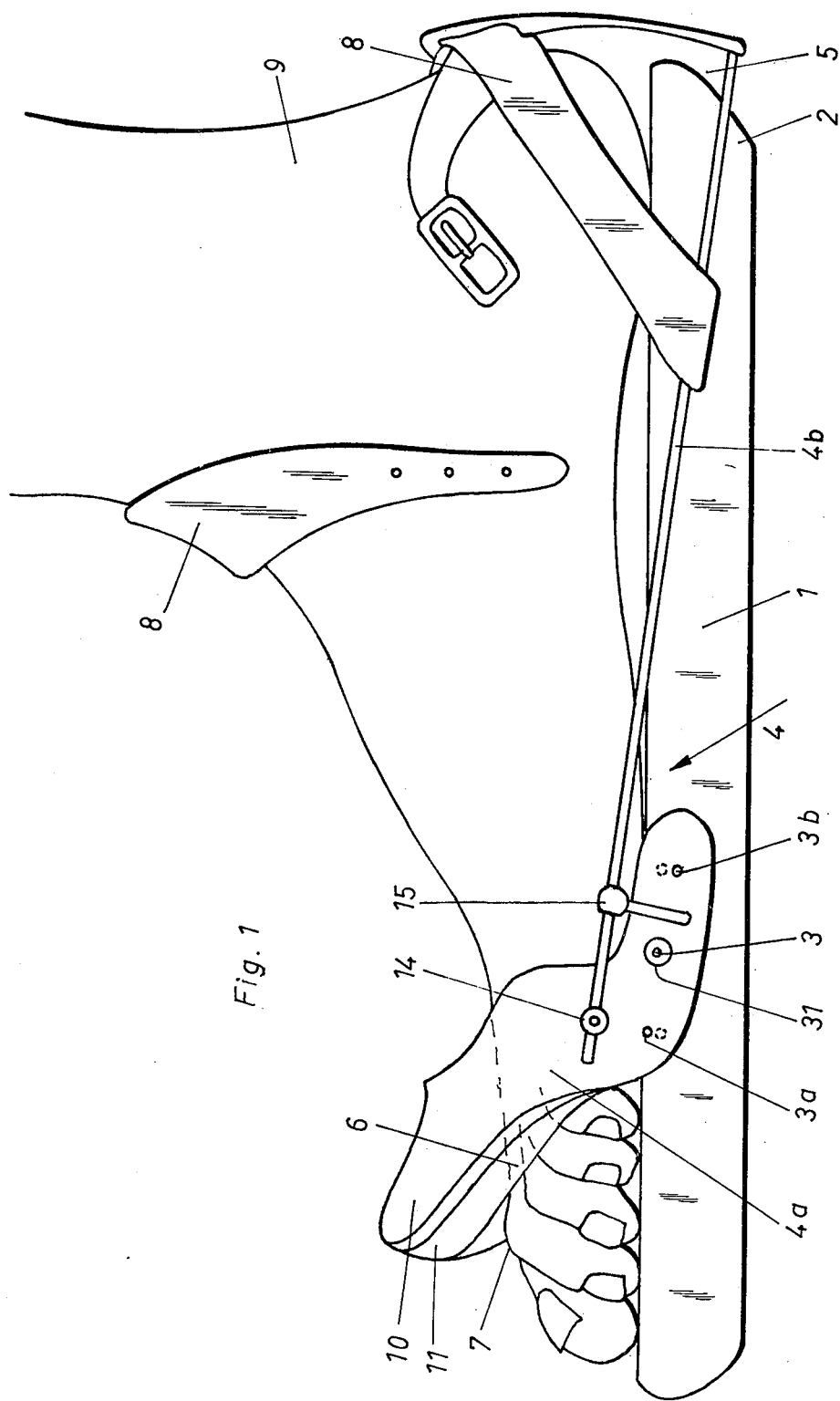
FIG. 1 is a side elevation of an embodiment of the present invention whereby the hammer-toes are not being stressed or pressed.

The inventive sandal comprises a solid sole 1 which may be slightly flexible in its rear heel section and may there be rounded upwards. A two-armed lever arrangement 4 is pivotally arranged at the sole at numeral 3. The lever arrangement 4 consists of a frontal lever arm 4a and a rearward lever arm 4b. A continuous frame which is closed in itself may serve as a lever arm arrangement (see FIG. 3), however, the present invention is not limited to this frame-shaped construction of the lever arrangement. Such a frame can be very simply constructed. For example, it may consist of a round self-resilient steel-wire of suitable stability and elasticity. This will effect a certain balance of the pressure exerted on the hammer-toes.

In order to obtain a greater effect of pressure, it is recommended that the frontal lever arm 4a is shorter than the rear lever arm 4b. This will produce an anatomically favorable position of the pivotal or turning axle 3, which, in accordance with the embodiment of FIGS. 1 and 2, as well as that of FIG. 3, is positioned in the frontal section of the sandal in such a manner so that when the foot rests on the sandal it will be located approximately at the level of the center bone of the foot or the adjacent basic joints of the toes. The pressure element 10, being in the form of a toe curvature plate which corrects the position of the toes, is mounted on the lever arm which extends forwardly of this pivotal axis. The toe curvature plate (pressure element 10), when the lever arrangement is shaped as a frame (FIG. 3), represents a portion of said frame. This curvature extends precisely over the basic joints 6 and the center joints 7 of the toes. It is provided at its bottom portion with padding 11 which can be worked or formed depending on the deformation of the toes.

The front lever arm 4a is fixedly connected with the rearward lever arm 4b at least during the use of the sandal. It may be of a single construction with the same, for example as in the above-explained structure of the lever arrangement as a closed-in frame according to the embodiment of FIG. 3.

Figure 2:
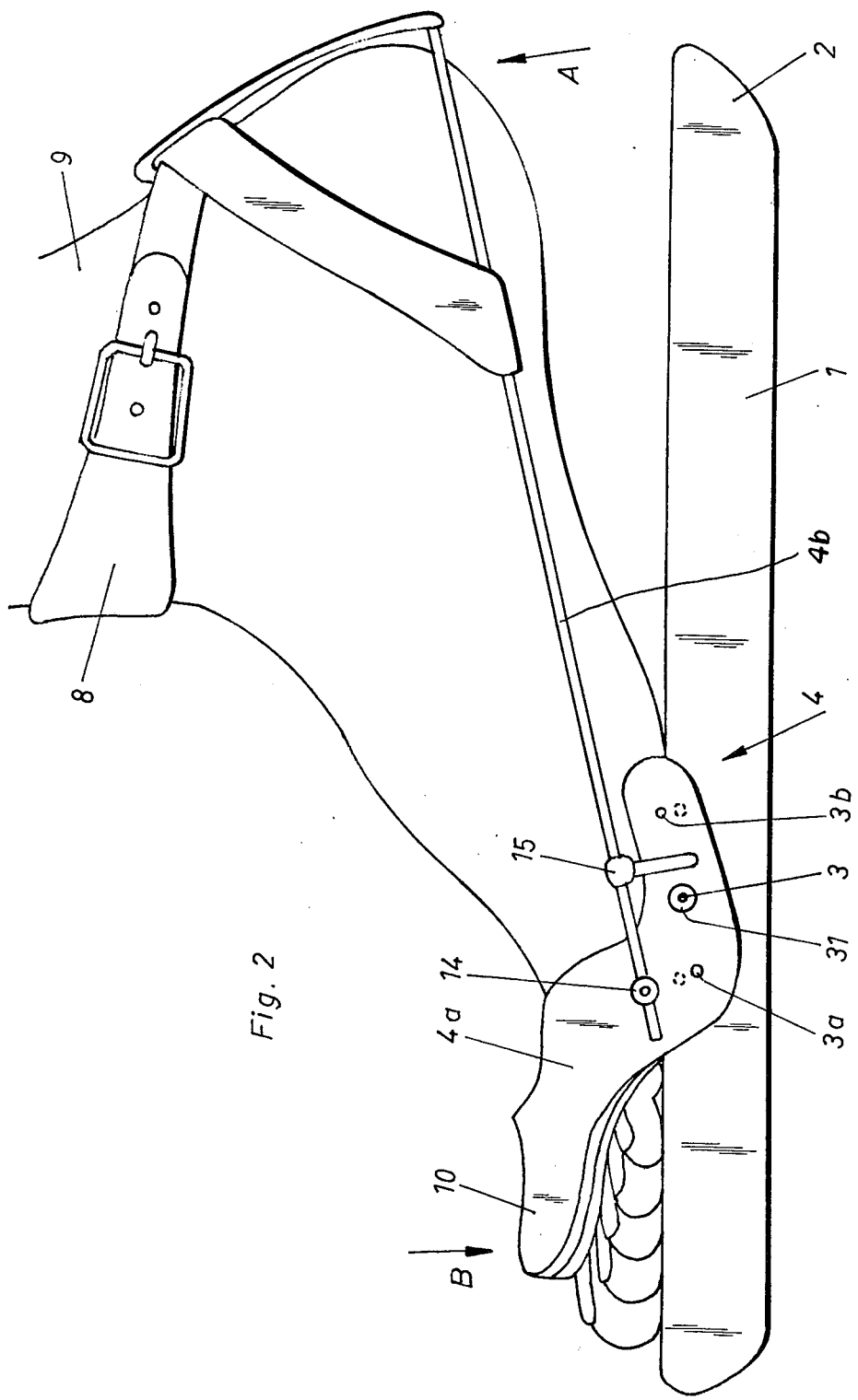
FIG. 2 is a side elevation according to FIG. 1, wherein the hammer-toes are stressed or pressed, in a stretched position before the ending of the rolling-up phase of the foot.
Figure 3:
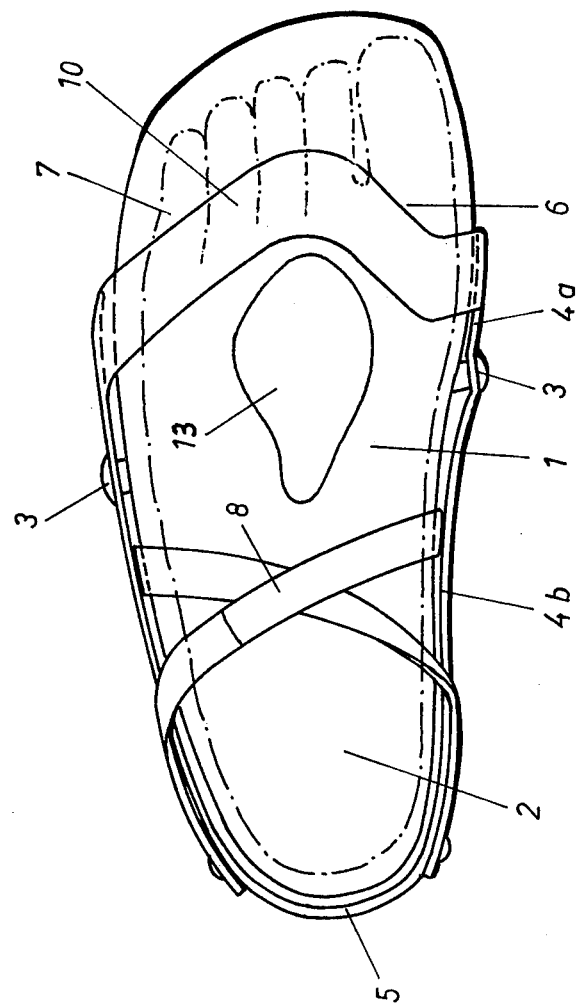
FIG. 3 is a top-elevational view of a further embodiment of the present invention.

In the embodiments of FIGS. 1 and 2, a steel wire coil forming in general the rearwrd lever arm 4b is pivotally connected at numeral 14 with the frontal lever arm 4a. Outwardly foldable hook-shaped holders or bolts 15 are provided. When these holders or bolts 15 engage the element 4b from above, the position of the latter to the frontal lever arm 4a is fixed and both lever arms form a frame which is fixed in itself and which is pivotable about the axis 3. When the bolting elements 15 are folded outwardly however, for the purpose of easier insertion of the foot underneath the curvature of the pressure element 10, the same may be provided wide enough upwards about the axis 3 to the sandal and about the axis 14 to the rearward lever arm 4b.

Straps 8 are fastened onto the rearward lever arm 4b, selectively over a heel cap 5, which is wound around the ankle 9 for forming the above-mentioned ankle-bandage, and may be held together fastening, for example, by means of miniature-hook and loop strips such as Velcro.

FIG. 1 shows the inventive sandal in a completely relaxed arrangement. A lifting upward of the rearward lever arm in the direction of arrow A into the position as seen in FIG. 2, on the basis of the formation and pivoting of the lever arm arrangement, will result in a pressing of the curvature of the pressure element 10 in the direction of arrow B on the basic joints 6 and the center joints 7 of the toes thus providing the correcting influence on these hammer-toes. It is therefore recommended that a portion of the sole area on which the toes are resting, be as smooth as possible so that during the afore-mentioned stretching process of the hammer-toes, the rubbing-resistance on the arches of the toes is reduced. By means of a correspondingly strong pulling of the ankle-bandage, it is possible to obtain a certain constant pressure of the curvature on the hammer-toe which is augmented by the intermittent pressure provided by the lifting upward of the heel. By means of the inventive combination of a constant pressure with an intermittent pressure there is provided a further possibility of variation of the dosage of desired treatment pressure. At the moment of the pulling-upwards of the foot, the lever effect and therewith the pressure on the toes is increased.

The longitudinal as well as the heel portion of the lever arrangement, or the frame formed thereby, are preferably located laterally and at a short distance adjacent the sole 1, whereby when the sandal is put on, and also when walking with the sandals, sufficient play of movement for the lever arrangement and for the foot is provided.

In the embodiment of FIGS. 1 and 2, are several holes 3, 3a and 3b, which are placed apart, one behind the other, in the lateral longitudinal portions of the lever arrangement, or in a closed frame 4 in longitudinal direction of said frame. A fastening screw or the like 31 may selectively be inserted into a corresponding opening of the sole 1, as indicated in the drawing by the broken line. The screw 31 forms the pivoting axis of the lever arrangement on the sole. It should be mentioned that an identical arrangement comprising three boreholes or holes 3, 3a, and 3b and a fastening screw 31 or the like are proposed on the other longitudinal side of the sandal (not shown in the drawing). The entire length of the lever arrangement, which comprises the lengths of the two lever arms 4a and 4b, however, remains unchanged. When the screws 31 are inserted into the frontal bore holes 3a, which are shown in the drawing at the left, the lifting upwards of the rearward lever arm 4b by a predetermined amount results in a relatively high force of pressure of the frontal lever arm 4a or of pressure element 10 on the toes. While the insertion of the screws 31 into the rearwardly positioned boreholes 3b, seen at the right in the drawing, results in a comparatively low pressure force of the pressure element 10 on the toes (based respectively on the lifting up of the rear lever arm 4b by the same amount). The drawing shows the arrangement of the screw 31 in the center bore hole 3, giving a medium pressure force of the pressure element 10 during the lifting upward of the rear lever arm 4b to the identical height.

The inventive object to provide a means in the frontal area of the sole for the purpose of correcting the X-position of the large toe, and to permit this means to become effective with the lowering of the pressure-element, e.g., simultaneously with the correction of the hammer-toes, may be realized in various ways by the instant invention.

Figure 4:
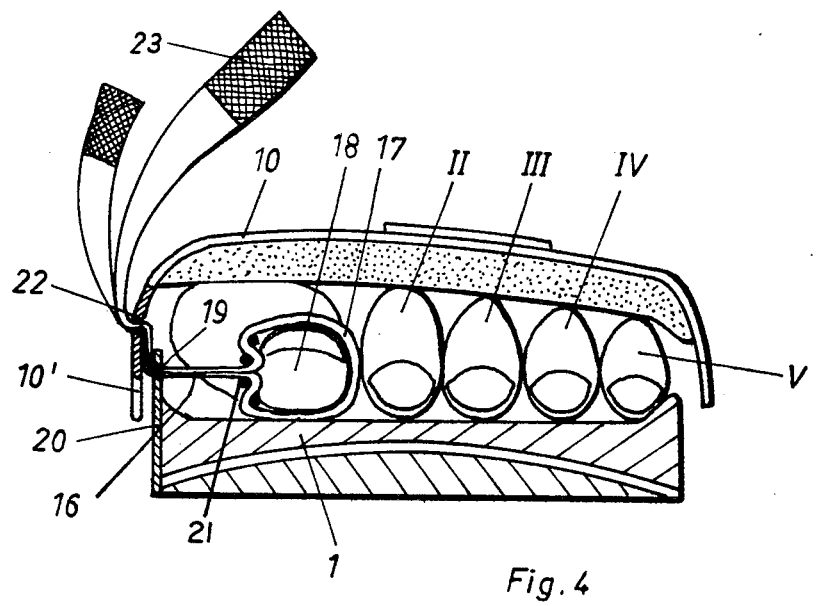
FIGS. 4 and 5, respectively, are front-elevational views of a further embodiment of the present invention with the pressure element in the two different positions.
Figure 5:
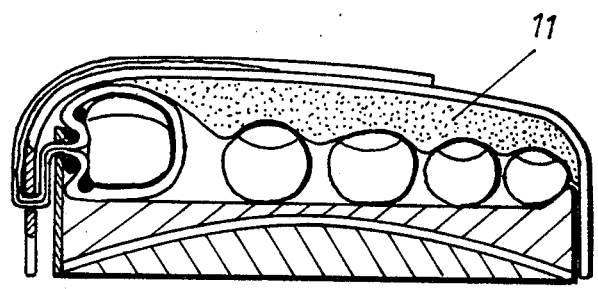

Thus, in the embodiment of FIGS. 4 and 5 there is proposed a strap 16 which is guided in a loop 17 around the large toe 18. The two portions of the strap 16 are then laying adjacent one another and are guided through the slot 19 of a boss or stop 20, which is mounted on the inside edge portion of the sandal 1. The loop 17 is provided with a supportive element 21 and is guided through the same. The supportive element 21 is preferably a steel wire or the like which in a serpentine fashion winds backward and forward. It protects the toe against cutting off circulation due to the pulling of the strap or the loop, and it holds together the strap or loop portions coming from the upper and the lower edge of the toe in a manner so that, as seen in the drawing, they come to lay close to each other and are able to slide through slot 19 without any needless friction. Since the loop section can be displaced relative to the support element, an adaptation of the loop-diameter to the respective thickness of the toe is thus possible. A further slot 22 through which the two end portions of strap 16 are guided, is located in the pressure element or holding bar 10. The slots 19 and 22 are positioned respectively in a manner so that they are somewhat congruent at a corresponding elevation of the pressure element 10, i.e., they are not displaced with respect to each other in longitudinal direction of the sandal. The longitudinal displacement of the strap 16 into the slots 19 and 22 enables the establishment of a selective basic or initial stress on the large toe 18 in an inward direction (medial), i.e., to the left, in FIG. 4. This position of the strap may either be retained by means of the strap itself, or by miniature hook and loop fastening means such as Velcro.

FIG. 4 shows the upwards lifted pressure element 10. In this position, the strap 16, with the exception of a possible initial stress, is released. When the pressure element 10 is moved by means of lifting the heel of the foot upwards into the position shown in FIG. 5, then the strap 16 is pulled through the slot 19 and the toe 18 is thereby pulled inwards. This pull/stress auguments intermittently somewhat the resulting and above-explained basic or initial stress. Simultaneously, the pressure element 10 or its padded portion 11 presses onto the remaining toes II-V, so that they are moved from the hammer position according to FIG. 4 into the stretched position as seen in FIG. 5.

It may be seen that with the present invention the correction of the X-toe together with the correction of the hammer-toes can be obtained by very simple means and without excessively high manufacturing costs.

Figure 6:
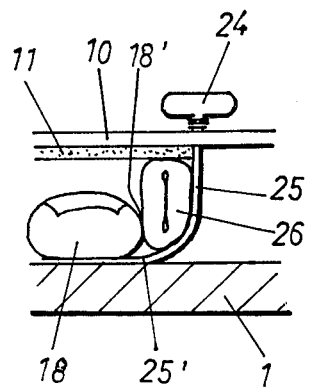
FIGS. 6 and 7 show respectively a further embodiment of the present invention, also in a front-elevational view, with the pressure element in the two different positions.
Figure 7:
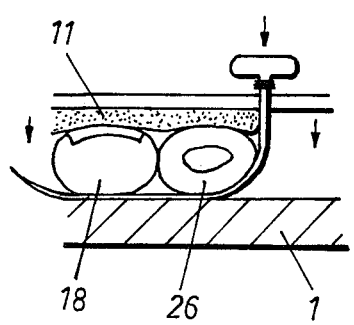
Figure 8:
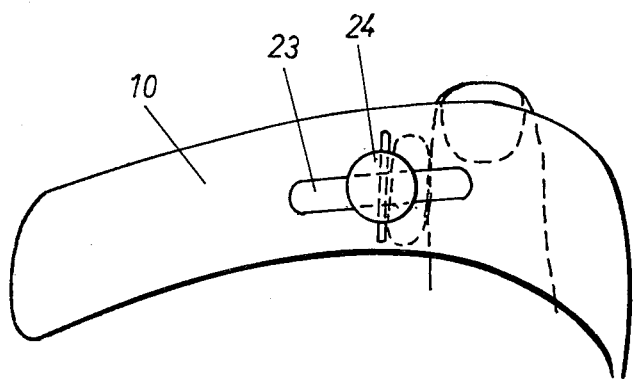
FIG. 8 is a top elevational view of the embodiment of FIGS. 6 and 7.

In the embodiment of FIGS. 6 to 8, a slot 23 in the pressure element or holding rod 10 extends in the longitudinal direction of the same, and into which is slidably arranged a push-handle 24. The respective position of the handle 24 to the slot 23, for example, may be affixed by a resilient stop block or by a threading. On the handle 24 there is mounted a toe-holder 25, for example a small synthetic material blade or a piece of metal, which in its perpendicular positioned portion is somewhat stronger and generally rigid, however, in its curved and lower transverse running portion 25' it is increasingly elastic. As soon as the holding rod 10 lowers itself, the elastic portion 25' pushes itself medially, i.e., inwardly underneath the large toe 18. At the bottom side of the holding rod 10 there is located the padding 11. At the underside of the holding rod 10 or the padding 11, a pressure element 26 consisting of an elastic material can be provided. This may be an elastic synthetic or rubber part or an oval-shaped thin steel-spring, an expansion member or the like which is shaped according to the scissor-mesh principle. The elastic synthetic or rubber part illustrated in this embodiment is formed so that it is somewhat oval when released, whereby the major axis of the oval is perpendicular to the sole of the sandal. It lies adjacent the outside edge 18' of the large toe 18 and is encircled by the holder 25 at its other longitudinal side and at its underside. This released (or relaxed) position of the parts is shown in FIG. 6.

When, by moving the heel of the foot upwards, a downward movement of the holder rod 10 and thus a downward pressure on the toes is performed, the element 26 takes on an oval shape in a manner so that the major axis of the oval shape is horizontal (see FIG. 7). Since the position of the mounting support of the toe holder 25 due to the fixation of the handle 24 remains unchanged, there results a movement of the large toe 18 inwards (medial), i.e., in FIG. 7, towards the left. When the pressure is removed, i.e., by lifting upwards of the holding rod 10, the toes 18 and the element 26 obtain again their initial position according to FIG. 6. It is seen that with the setting of the position of the handle 24 in the longitudinal direction of the holding rod 10, the basic or initial stress is produced, but with the downward movement of the holding rod 10 there is performed a traction force on the large toe which is augmenting and intermittent to this basic pressure.

Figure 9:
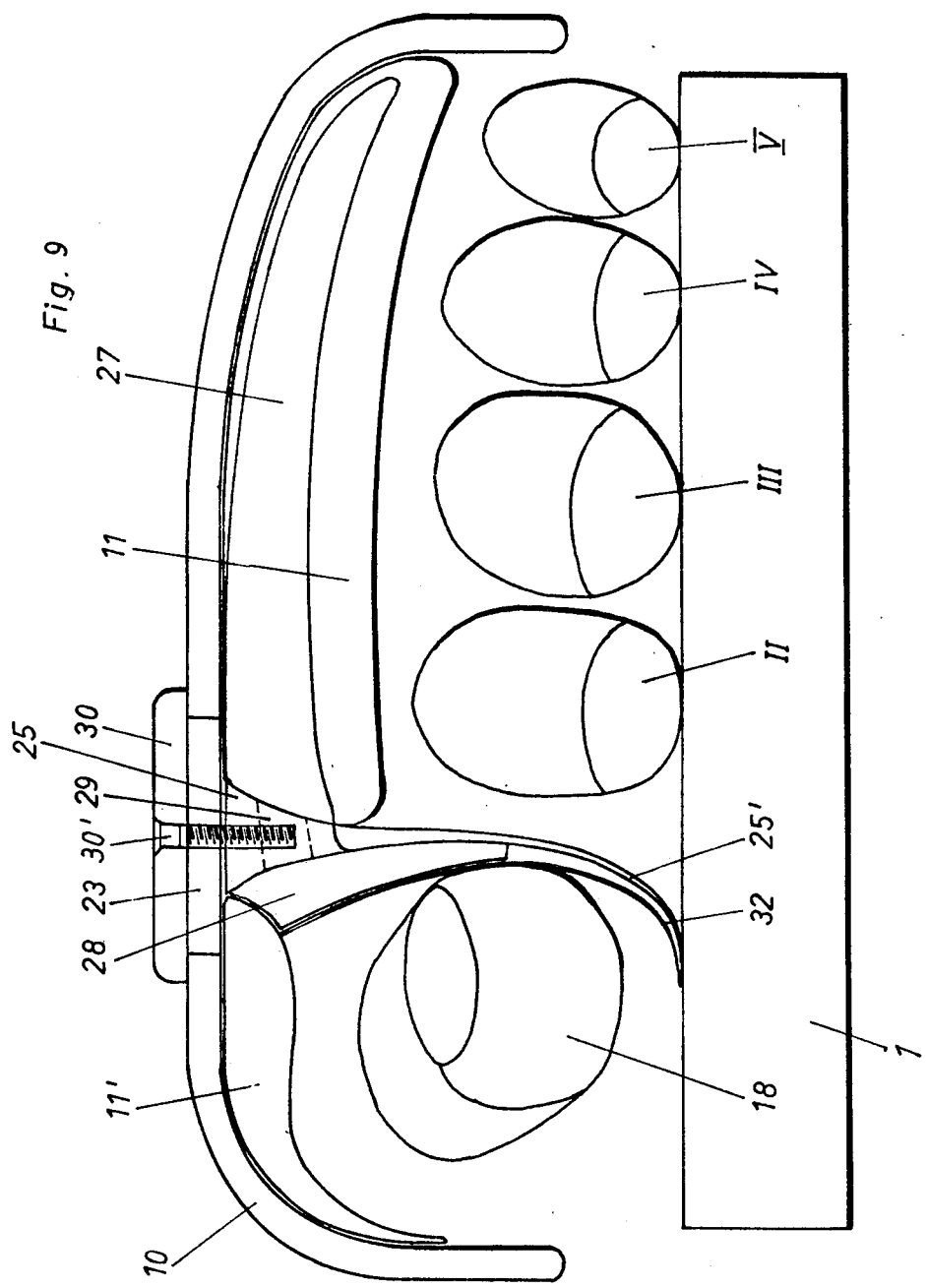
FIGS. 9 and 10 represent a fourth embodiment of the present invention, with the pressure element in the two different positions.
Figure 10:
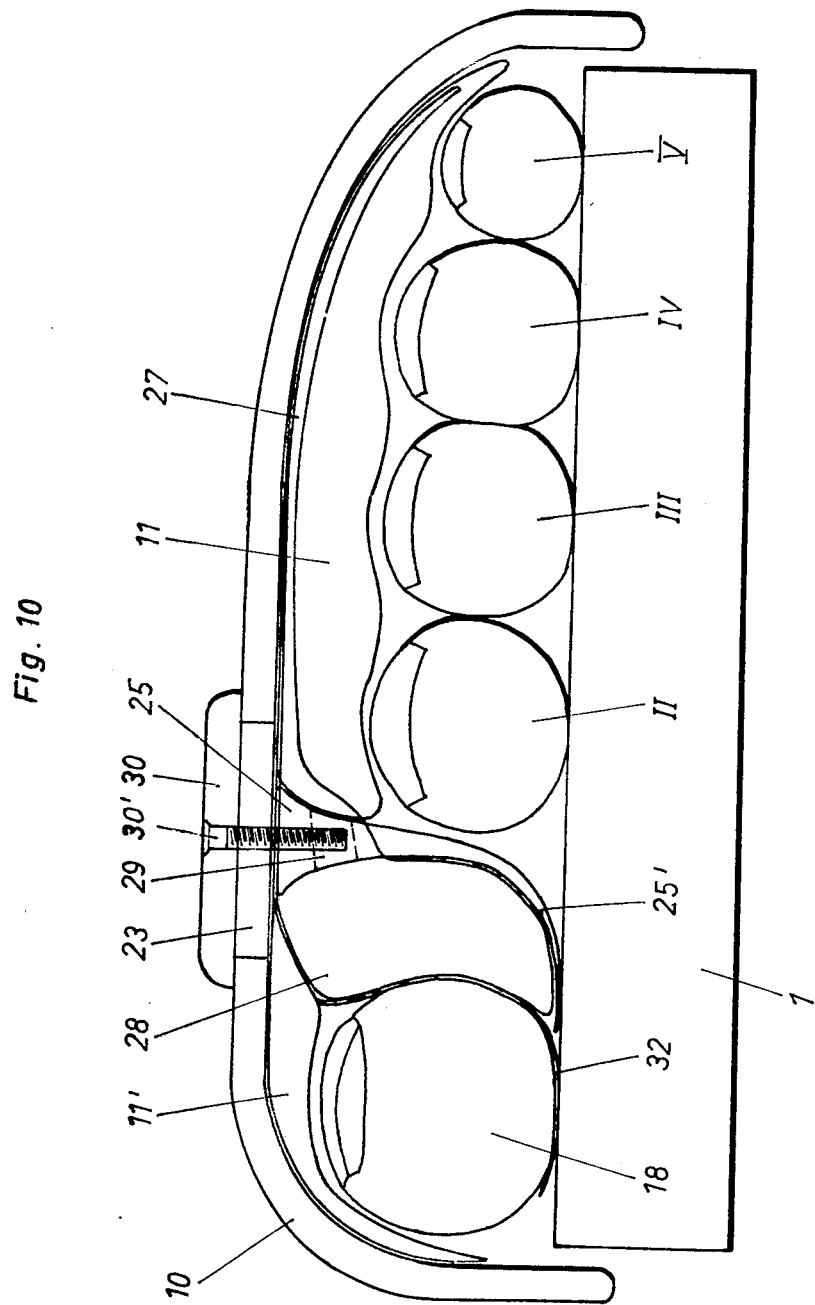

In the embodiment of FIGS. 9 and 10, FIG. 9 illustrates the relaxed position, i.e., the holding rod 10 is not pushed downwards, while FIG. 10 shows the stressed position (toe is pressed downwards). In the latter-mentioned position, the pressure of the holding rod 10 is transmitted inwards (medial) to the movement of the large toe 18 by means of a system cooperating with a pressure medium, i.e., to the left in the drawing. This system consists of a first, compressible chamber 27 and a second chamber 28, which in its function corresponds with the element 26 of the embodiment illustrated in FIGS. 6 and 7, and is connected with the first chamber 27 by means of an opening 29. The system of chambers 27, 28 and the opening 29 in this embodiment is filled to about 3/5 of its total capacity with air. Instead of such a pneumatic system, a hydraulic system can be provided which is filled to about 3/5 of capacity with fluid, and which, in principle, would function precisely in the same manner. In the preferred pneumatic embodiment a thin, strongly-flexible synthetic material or also a thin, elastic rubber material may be used for the chambers 27, 28.

The first chamber 27 is located above the toes II to V and is compressed by pressing the holding rod 10 downwards. Preferably, this chamber is formed by the foam rubber padding itself, in that said padding is being provided with a hollow space during its manufacture, which represents the chamber 27. The chamber formed by means of a bag consisting of a rubber or of a synthetic material could also be foamed over by the padding-material.

The opening 29 is located in the cavity or borehole of the fixed portion of the toe holder or toe-guiding plate 25, the lower, elastic portion of which is herein enumerated with 25'.

The second chamber 28 is filled with the medium (air or fluid) when the holding rod 10 is pressed downwards due to the compression of the first chamber 27, and the large toe 18 is thereby pushed to the left (see FIG. 10). The toe guiding plate 25 also prevents the chamber 28 from moving in the direction of the toe 11. If the holding rod 10 is again moved into the released position according to FIG. 9, the X-toe 18 presses the chamber 28 together again. This may be accomplished also by the elasticity of the chamber 28. The ratio of the volume of the chamber 27 to chamber 28 in this embodiment is 3:2 respectively.

Also in this embodiment, portion 25' slides below the large toe 18 when the holding plate 10 is pushed downwards. An adjusting means on the toe holder or toe-guiding plate 25 for adjusting the holder in the longitudinal direction of the holding bar 10 is also shown in this embodiment. This comprises a slot 23 in which the fixation of the respective set position is made by one or more screws 29 which penetrate the one or more slots 23 and are screwed into corresponding threaded holes of the upper portion 25 of toe holder 25. There can furthermore be provided an additional elastic plate 32 at the inside of chamber 28, which engages the toe 18 from below and which prevents the large toe getting below the chamber 28.

The padding 11 is preferably so formed that the chamber 27 will be located in the upper portion, namely, that the greatest mass of padding is located between the chamber 27 and the toes II to V. An additional padded section 11' can be provided above the large toe. Both padded sections may be fastened in a selective manner at the bottom side of the holding rod 10 and, preferably, be glued thereto.

Also this embodiment effects with the upward-lifting of the heel of the foot, especially during walking, the holding rod 10 is pushed downward, and that the hammer-toes II to V are thereby stretched and simultaneously a medial movement of the large toe 18 is made. The correction is made intermittently. This may be augmented also by a constant pre-stressing on the basis of the respective adjusting of the adjustment means 23, 29 in the longitudinal direction of the holding rod 10.

It is of course understood that the characteristics and functions as described with respect to FIGS. 1 to 3 may be provided or fulfilled accordingly in the embodiments of FIGS. 4 to 10.

With reference to the illustration in FIGS. 1 to 3, it will here also be pointed out that at the movement of an increase in stress, i.e., the rolling up of the foot, there may develop a widening of the frontal foot portion. In order to prevent this, the frontal foot portion is covered at both its sides by a bowl-shaped arching 12 of the sole which is placed on the inside length of the sandal and the outside length of the sandal. This serves at the inside length of the sandal firstly as a pivotal point (Hypomochlion) for correcting the X-toes. In the manufacture of the sandal, there may be considered deviating widths of the frontal portion of feet by providing various strengths of paddings of these archings inwardly and outwardly.

The sole is provided at its contact area with a longitudinal and transverse arching 13, as schematically indicated. During stressing of the foot, this will have a corrective influence on the formation of a splay-foot and serves simultaneously as a means of resistance for the foot during the stretching of the hammer-toes.

For this purpose of obtaining an increased protection against a medial sliding (inwardly) or against developments of pressure, especially at the frontal, inner portion of the foot, a strap-shaped holder means for the front section of the foot may be provided. The stretching of this strap holder may be adjusted selectively. The aforementioned characteristics are not shown in the drawing.

Much value is placed in the afore-mentioned transverse-arching on a retrocapitular, i.e., a support of the foot located behind the top of the center foot bone by means of a wide splay-foot pelotte. The correction of the X-toe may also be made by means of a device which is built into the sole of the sandal and which is activated not as in the above-noted embodiment by means of the holding rod 10, but by the foot itself when the foot pushes downwards. This is also made simultaneously with the correction of the hammer-toes.

Figure 11:
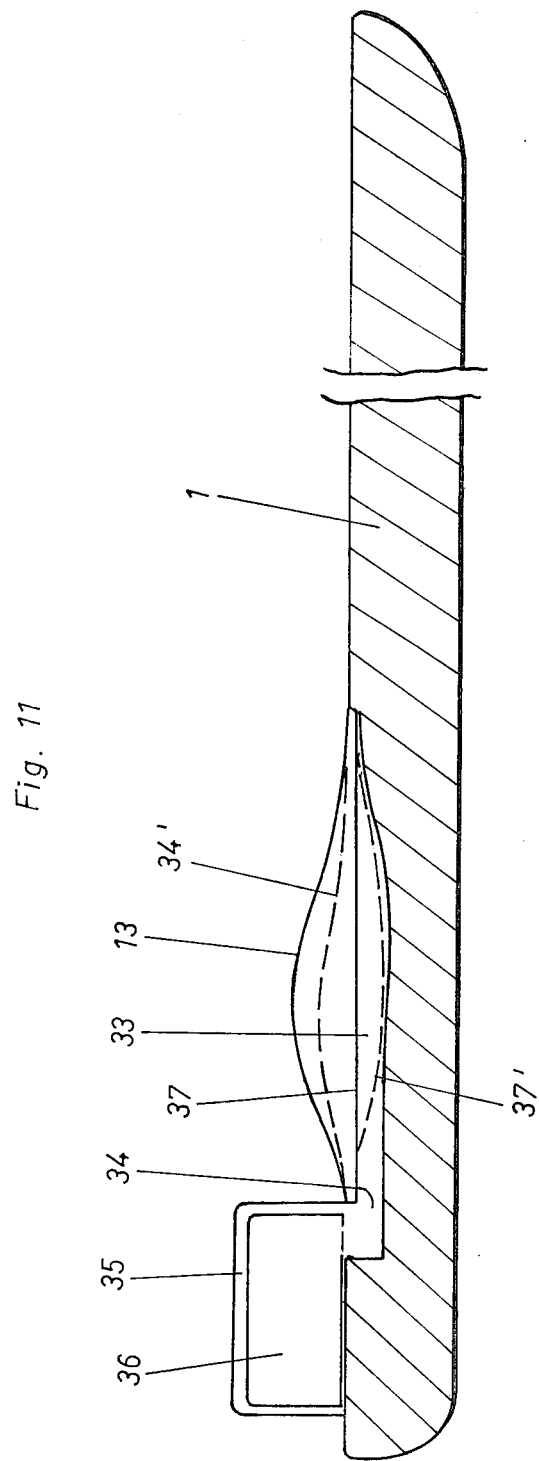
FIGS. 11, 12 and 13 to 15 illustrate a further embodiment of the present invention.
Figure 12:
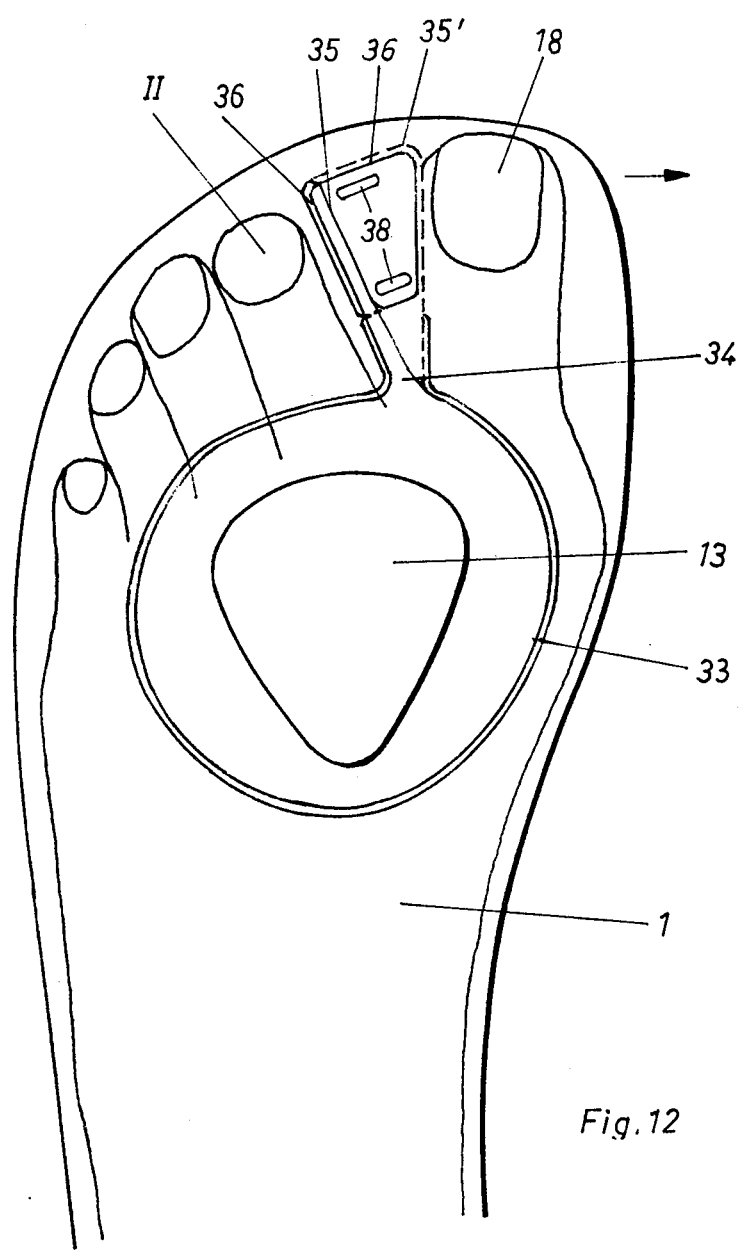

In the embodiments of FIGS. 11 and 12, FIG. 11 shows a longitudinal cross-section through the portions of the sandal being of interest here, and FIG. 12 illustrates the pertinent top view. In the area of the sole 1 which is located below the front portion of the foot when same is placed onto the sole a first pressure chamber 33 is provided which is in communication with a second pressure chamber 35 by means of a feed pipe 34. Above the first chamber 33 there is located the flexible splay-foot pelotte 13, which is pushed downwards by the pressure of the foot. Between the second pressure chamber 35 and the toe II a toe-guiding rod, or toe-holder 36 is provided, which, for example, is mounted on the sole (see also FIG. 12). The two pressure chambers consist of an elastic material, for example rubber or a synthetic material. The pressure chambers, as in the embodiment of FIGS. 9, 10, may be filled with air or a fluid. In FIG. 11 there is shown the relaxed position of the upper surface of the sole and the upper surface of chamber 37 which are not under the pressure of the foot, shown by the solid line. The stressed position, namely, the position being under the pressure of the foot or the weight of the body, is indicated by numerals 34' or 37' and the broken line. Analogously in FIG. 12, the relaxed position of the second pressure chamber 35 is shown by the solid line and its stressed, i.e., stretched, position is indicated with numeral 35' and the broken line. In order to clearly construct the illustration without confusing the same, the X-toe 18 is shown only in the position in which it is pushed by the second pressure chamber 35' to the medial, in the direction of the arrow. The toe-guiding bar 36 is provided with two slot-guides 45 with which it is adjustable to the sole in the direction of the arrow, and is affixed in the respective set position by means of screws which penetrate the slots 45. The large toe 18 can be provided with a predetermined initial or basic stress in the direction of the arrow. Also here, an intermittent X-toe correction can augment a constant initial stress.

Figure 13:
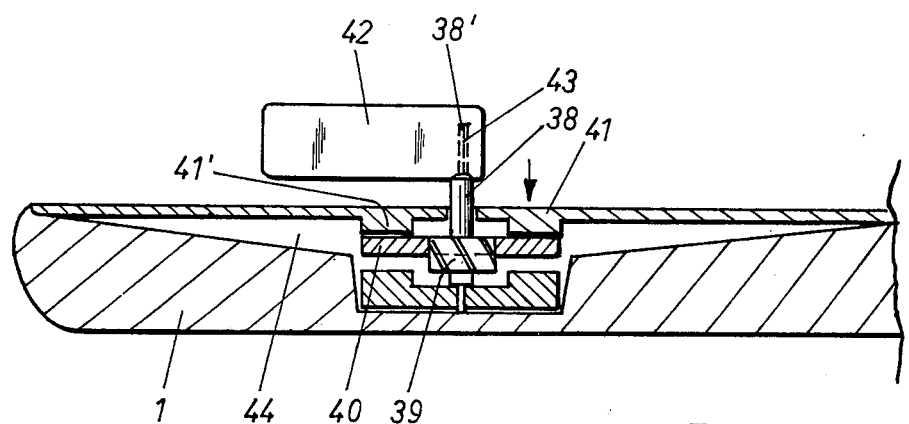
Figure 14:
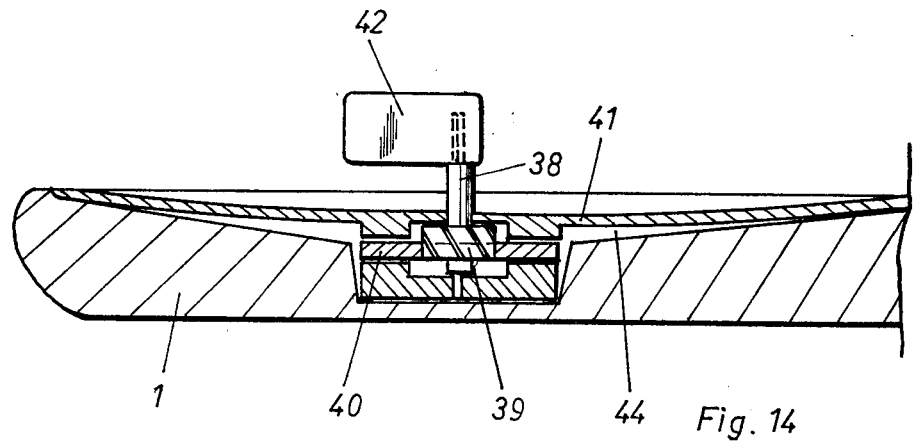
Figure 15:
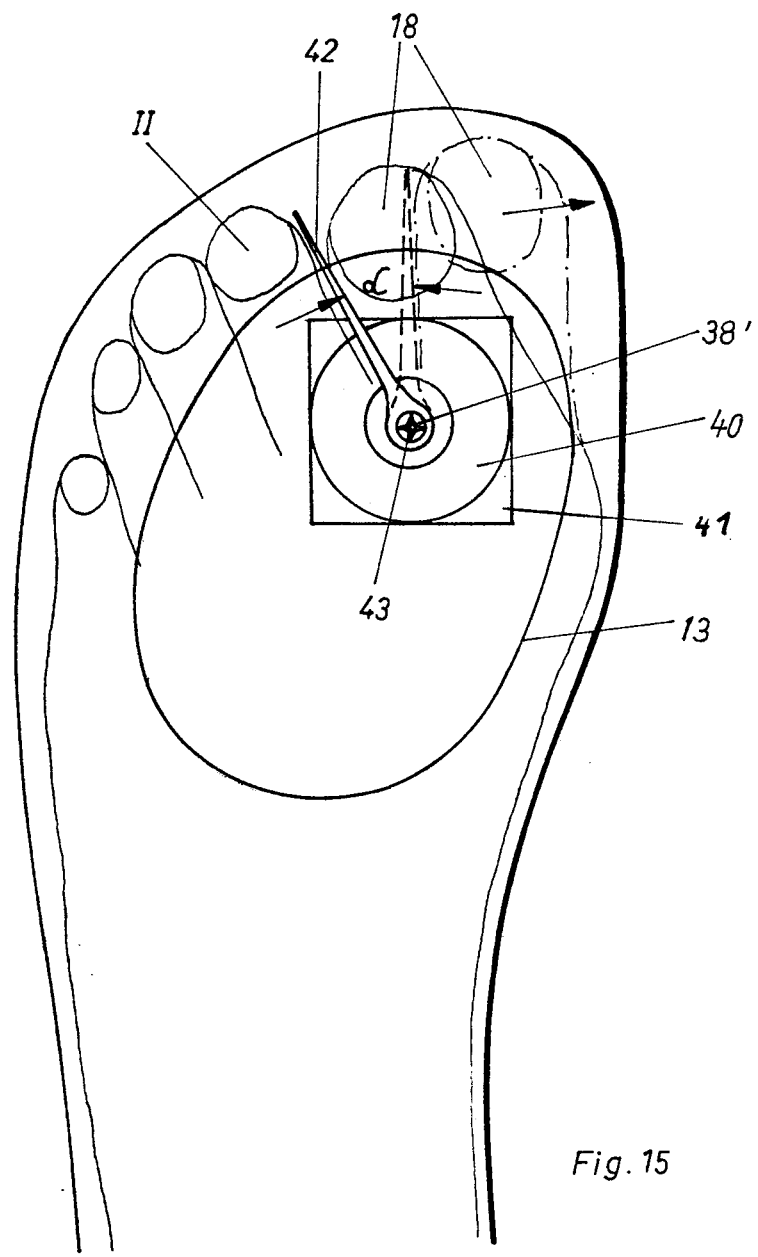

The embodiment of FIGS. 13 to 15 shows a mechanical means for the same purpose. Namely, in FIGS. 13 and 14 show a cross-section through the front portion of sole 1 at an unstressed (FIG. 13) and a stressed (FIG. 14) condition, while FIG. 15 is the inherent top view thereof. In FIGS. 12 and 15 are illustrated some portions for a better overview by means of a broken line which are not visible in top view.

In the embodiment of FIGS. 13 to 15 there is an arrangement proposed in the sole below the area of the front portion of the foot when same is emplaced on the sole 1, which operates in accordance with the principle of a drill. A vertically-positioned screw 38 is provided with a steep-spiral threaded portion 39, into which engages a nut 40 having a corresponding threaded inner portion. The nut 40 is plate-shaped and is located below a flexible portion 41 of the sole, which is freely movable relative to the screw 38, resting on the nut-plate 40. The portion 41, due to its flexibility, is movable from the front portion of the foot in the direction of the arrow. The screw 38 is located between the large toe 18 and toe II, between which is also provided a wing-shaped toe-holder means 42, which is placed onto the upper end of the screw 38' and is non-rotatably connected with the same. A pushing downwards of the plate-shaped nut 40 by means of the front portion of the foot produces a rotation of the screw 38 which is rotatable in its position on the basis of the interengaging steep-spiral threaded portion, and thus produces a rotation inwardly of the toe-holder means 42 through an angle α (see FIG. 15). This angle α is preferably 30°. In this way, with each downward-pressure of the foot an intermittent correction of the X-position of the large toe 18 is preformed, simultaneously with the correction of the hammer-toe by means of the pressure (or holding) rod 10. For reasons of a better understanding, the pressure element 10 which is existing in the embodiments, is not shown in FIGS. 11, 12, and 13 to 15. In the instant embodiment, the plate-shaped threaded nut 40 is non-rotatable relative to the sole, i.e., it is not able to turn in its plane, while the screw 38 is rotatably positioned and is carrying the toe-holder means 42. In principle, the arrangement could also be reversed, whereby the nut 40 is rotatable relative to the sole and the screw, and carries the toe-holder means via a suitable connecting member.

The upper portion of the screw 38' may be provided with splines or teeth 43, over which are fitted corresponding counter-teeth of the bore holes 42 in the holder means. With this, it will be possible to emplace the holder means onto the same when the sandal is not stressed, into variously angled positions relative to the screw 38,38'. Thus, the large toe 18 can be provided with a certain amount of initial or basic stress by means of the holder element 42 in the sense of a medial movement according to the arrow in FIG. 15.

In order for the sole to spring back when the pressure from the foot is removed, there may be proposed an elastic filling of a padding in the hollow space 44 of the upper surface side of the sole. Furthermore, the upper side of the sole may be provided with an annular pressure circle 41' to improve the pressure transmission to the nut 40.

What is claimed is:

1. An orthopedic sandal for a foot comprising
a sole having a longitudinal axis and a front and rear end, a lever arrangement mounted on said sole for pivotal movement about a horizontal axis, said horizontal axis being transverse to said longitudinal axis,
said horizontal axis being positioned in said sole such that when a foot rests on said sole with its heel near said rear end of said sole and its toes near said front end of said sole, said horizontal axis is adjacent the ball of the foot, said lever arrangement having a first arm extending from a point adjacent said horizontal axis to a point adjacent said front end of said sole, said first arm having integral therewith a pressure element extending over the top of said sole, said pressure element being positioned such that when a foot rests on said sole with its heel near said rear end of said sole and its toes near said front end of said sole, said pressure element is over the basic joints and the center joints of the toes, said lever arrangement having a second arm extending from a point adjacent said horizontal axis to a point adjacent the rear end of said sole, means for attaching said second arm to the rear portion of a foot,
said first and second arms being connected to one another such that when a foot rests on said sole with its heel near said rear end of said sole and its toes near said front end of said sole and said attachment means is attached to the rear portion of the foot and the rearward portion of the foot is lifted from said sole, said second arm is raised causing said pressure element to be pressed onto the basic joints and the center joints to the toes.

2. The sandal according to claim 1 wherein the horizontal axis of the lever arrangement is to be fixedly connected to the sole.

3. The sandal according to claim 1, wherein said first arm is shorter than said second arm.

4. The sandal according to claim 1, wherein said pressure element is in the form of a holding bar, the form and position of said bar corresponding with the position of the emplaced foot, and is provided with a padding means on its bottom portion.

5. The sandal according to one of claims 1, 3 or 4, wherein the lever arrangement consists of a fixed, but elastically resilient material.

6. The sandal according to claim 1, wherein the lever arrangement comprises an elongated, in itself closed, frame, which at the side of the toes forms a holding rod and at the side of the heel is provided with said means for fastening it with the rearward portion of the foot.

7. The sandal according to claim 1, wherein said first and second arms are pivotably connected with each other, and said arrangement further has a bolting element provided between the two lever arms which is selectively releasable from its bolting position wherein the two arms are coupled into one fixed unit.

8. The sandal according to one of claims 1, 3, 4, 6 or 7, further comprising pressure changing means for adjusting the position of the pivot point of the lever arrangement in the longitudinal direction of the sole, while the entire length of the lever arrangement remains unchanged.

9. The sandal according to claim 8, wherein said pressure changing means comprises a plurality of holes positioned in a row in the longitudinal direction in the lever arrangement, through which is insertable a pivot pin means, forming said horizontal axis and being fastened in said sole of the sandal.

10. The sandal according to claim 1, wherein the sandal is provided with a smooth gliding area for the heads of the toes representing the area which serves for the enplacement of the foot.

11. The sandal according to claim 1, further comprising a means for correcting the X-position (Hallux Valgus) of the large toe in the frontal area of the sandal, and said means being in functional connection with said pressure element such that a downward movement of the pressure element effects a movement of the large toe inwardly (medial).

12. The sandal according to claim 11, wherein the means for the correction of the X-toe is constructed in such a manner so that in addition to an intermittent correction a constant pulling inwardly (medial) is performed on this X-toe.

13. The sandal according to claim 12, wherein an said correcting means is adjustable loop which surrounds the large toe and which is fastened to said pressure element.

14. The sandal according to claim 13, wherein said loop is provided with a supportive element which protects the toe against a cut-off of circulation, and which holds together and guides the portions of the loop coming from the inner edge of the toe joining the same together to form a strap.

15. The sandal according to claim 14, further comprising an upwardly extending stop member with a slot for the guiding therethrough of said strap affixed to the inside portion of the sole, and a further slot for guiding the strap therethrough provided on the pressure element, the two slots being vertically aligned so that they are approximately congruent at all positions of the pressure element.

16. The sandal according to one of claims 14 or 15, wherein said strap is longitudinally adjustably arranged to lie in position on the pressure element, and a fastening means is provided to retain the strap in fixed position.

17. The sandal according to claim 12, further comprising a predetermined elastic element associated with said pressure element, which elastic element is directed downwardly and is in engaging position with the large toe, and which elastic element expands and pushes the large toe inwardly during the downwards movement of the pressure element.

18. The sandal according to claim 17, further comprising a holding device mounted on the pressure element which encircles the elastic element at its outer- and under-side, said holder device in its upper area being substantially rigid and in the area which cooperates with the elastic element being elastic.

19. The sandal according to claim 17, wherein the elastic element has a somewhat oval cross section; when the pressure element is lifted off, the major axis of the oval is vertical and in the stressed condition when the pressure element is lowered, the major axis of the oval extends somewhat horizontal.

20. The sandal according to one of claims 18 or 19, wherein the holding device is slidably arranged in a slot of the pressure element and is stationarily arrangeable in the respective position, whereby the slot extends somewhat in the longitudinal direction of the pressure element, somewhat transverse to the longitudinal direction of the foot.

21. The sandal according to one of claims 17 or 18, further comprising a pneumatically or hydraulically operating system having a first pressure chamber which is activated by a second pressure chamber which forms the elastic element and which affects the large toe, said second pressure chamber being in communication with the first chamber through an opening which carries the pressure medium, and whereby a pressure increase in the first chamber results in a form-change of the second chamber which moves the large toe inwardly, and including means for retaining the second chamber in a fixed position at its outer side.

22. The sandal according to claim 21, wherein the first pressure chamber is built into said pressure element.

23. The sandal according to claim 1, further comprising in the frontal area of the sole, a means for correcting the X-position (Hallux Valgus) of the large toe, which can be brought into the corrective position comprising a device which is activated by the pressure of the foot onto the sole of the sandal.

24. The sandal according to claim 23, wherein said device comprises a first pressure chamber in the sole below the front portion of the emplaced foot which pressure chamber is compressible by means of the pressure of the foot, and being in communication with a second pressure chamber by means of a connecting pipe, said second pressure chamber being located between the large toe and the toe and being compressed by means of the pressure of the large toe, whereby the medium flowing from the first pressure chamber into the second pressure chamber under the weight of the foot causes said second pressure chamber to extend in the direction of the large toe and move the toe medial.

25. The sandal according to claim 23, wherein said device comprises a screw with a steep-spiral threading mounted in the sole below the forefoot, and a nut having a corresponding threaded portion and engaging into said threading; a means for transmitting the foot-pressure to the nut or the screw and moving these parts relative to each other; and a corrective device mounted on the nut or screw which is tiltable on the basis of the relative movement about the axis of the screw, whereby said corrective device engages the outside of the large toe.

26. The sandal according to one of claims 23 to 25, wherein a basic or initial stress on the large toe in the medial direction can be made by a toe-holder or toe-holder plate.

27. The sandal according to one of claims 1, 11, or 13, further comprising a longitudinal and a transverse arching for the correction of the sunken arches and splayfoot on the sole in the area of emplacement of the foot.

* * * * *